United States Patent [19]
Turschmid et al.

[11] Patent Number: 6,013,512
[45] Date of Patent: Jan. 11, 2000

[54] METHOD FOR SCRUBBING GASEOUS EMISSIONS USING BACTERIA

[76] Inventors: Krzysztof H. Turschmid, 2423 Brantford Dr., Charlotte, N.C. 28210; Krishnamurthy Sridhar, 13 E Hawthorne Woods, Deptford, N.J. 08096; Douglas P. DuFaux, 4917-4 Wateroak Rd., Charlotte, N.C. 28211

[21] Appl. No.: 08/868,220

[22] Filed: Jun. 3, 1997

Related U.S. Application Data

[60] Provisional application No. 60/029,869, Nov. 6, 1996.

[51] Int. Cl.⁷ ...................................................... C12S 5/00
[52] U.S. Cl. ........................... 435/266; 435/262; 210/615
[58] Field of Search ................................ 435/262, 262.5, 435/266; 210/610, 615, 150, 151; 423/235, 237, 238, 245.1, 245.2; 422/1, 4, 120, 122, 124, 168, 169

[56] References Cited

U.S. PATENT DOCUMENTS

| | | |
|---|---|---|
| 1,701,825 | 2/1929 | Seil . |
| 3,824,151 | 7/1974 | Iijima et al. . |
| 3,824,185 | 7/1974 | Caldwell et al. . |
| 4,046,921 | 9/1977 | Akao et al. . |
| 4,723,968 | 2/1988 | Schippert et al. . |
| 4,806,148 | 2/1989 | Ottengraf et al. . |
| 4,892,818 | 1/1990 | Ramp . |
| 4,968,622 | 11/1990 | Berzaczy et al. . |
| 5,017,351 | 5/1991 | Rafson . |
| 5,077,025 | 12/1991 | Glass . |
| 5,246,584 | 9/1993 | Donaldson et al. . |
| 5,248,613 | 9/1993 | Roubicek . |
| 5,409,834 | 4/1995 | Birdwell . |
| 5,503,738 | 4/1996 | DeFillippi et al. . |
| 5,681,470 | 10/1997 | Safi . |

FOREIGN PATENT DOCUMENTS

| | | | |
|---|---|---|---|
| 0 442 078 | 8/1991 | European Pat. Off. ............... | 435/266 |
| 0 528 110 | 2/1993 | European Pat. Off. . | |
| 40 17 230 | 12/1991 | Germany ............................... | 435/266 |
| 50-69279 | 6/1975 | Japan ..................................... | 435/266 |
| 52-27061 | 3/1977 | Japan ..................................... | 435/266 |
| 61-64316 | 4/1986 | Japan ..................................... | 435/266 |
| 4-27415 | 1/1992 | Japan . | |

*Primary Examiner*—William H. Beisner
*Attorney, Agent, or Firm*—Dority & Manning, P.A.

[57] ABSTRACT

An apparatus and method for control and treatment of ammonia ($NH_3$), oxides of nitrogen ($NO_x$) or volatile organic compounds (VOC) emitted in a gaseous form from various processes where these compounds are used, present or formed. The gaseous emissions may be comprised of $NH_3$, $NO_x$ or VOC individually or as a mixture of these compounds and other gaseous substances such as air, organic vapors and other organic or inorganic gases. The control and treatment method involves simultaneous liquid scrubbing and biochemical decomposition of $NH_3$, $NO_x$ or VOC or a combination thereof.

21 Claims, 9 Drawing Sheets

Process Flow Diagram for BioScrubber Pilot Test

FIG. 10

Process Flow Diagram for BioScrubber VOC & Ammonia Pilot Test

METHOD FOR SCRUBBING GASEOUS EMISSIONS USING BACTERIA

The present application claims the benefit of Provisional Application filed on Nov. 6, 1996 and having U.S. Ser. No. 60/029,869.

FIELD OF THE INVENTION

The present invention generally relates to a process and apparatus for the removal of gaseous pollutants from a waste gas stream. More particularly, the present invention is directed to a process and apparatus for removing ammonia and oxides of nitrogen from waste gas streams by contacting the waste gas stream with an aqueous suspension containing microorganisms. In one embodiment, the waste gas stream can also contain volatile organic compounds which are also removed from the waste gas stream by the aqueous suspension of microorganisms. In an alternative embodiment, the present invention is further directed to a process and apparatus for simultaneously removing pollutants from a waste gas stream and a waste water stream using microorganisms.

BACKGROUND OF THE INVENTION

This invention relates to an apparatus and method for control of gaseous emissions of ammonia ($NH_3$), oxides of nitrogen ($NO_x$) or volatile organic compounds (VOC) from various processes where these compounds are used, present or formed.

$NH_3$, $NO_x$ or VOC are frequently used in industrial processes as reactants or they may be formed as a result of chemical or biochemical reactions. These compounds, which are frequently vented from the process, can adversely impact air quality. Emissions of these compounds are, therefore, frequently regulated by the government and controlled by application of a variety of technologies. Some of the most frequently used technologies utilize water, sodium hydroxide or sulfuric acid scrubbing processes.

In the case of water scrubbing, there is a limitation resulting from the water becoming saturated with the dissolved pollutant. This inhibits further absorption of the pollutant by the water. In many situations, water solutions of sulfuric acid or sodium hydroxide are used as the scrubbing solutions to improve the solubility of the pollutant. However, the scrubbing solution may still become saturated with the dissolved pollutant inhibiting further absorption.

In the present invention, the scrubbing solution contains biological media which metabolizes the pollutant at a rate such that the scrubbing solution does not become saturated with the absorbed pollutant. As the absorption rate of the pollutant by the scrubbing solution is proportional to the difference between the concentration of the pollutant in the gas phase and the absorbed phase, this invention allows for high absorption rates of gaseous pollutants.

A prior art biochemical process, used to control emissions of vapors of VOC, is based on an attached growth bioreactor model where a reactor is filled with packing such as for example granular activated carbon which in turn promotes biological growth on the surface of the carbon. The gases pass around the packing covered with the biological growth and are absorbed and treated.

Unlike this prior art process, the present invention utilizes suspended growth of the biological process rather than attached growth. This difference results in a reduced sensitivity to pollutant concentration fluctuations in the process gas stream entering the bioscrubber. This is accomplished in the invention by maintaining an inventory of microorganisms in the bioreactor section of the bioscrubber and adjustment of the availability of the microorganisms to treat the gaseous emissions.

Aqueous suspensions containing microorganisms have been used in the past to treat waste gas streams. For instance, U.S. Pat. No. 4,723,968 to Schippert, et al. discloses a method and apparatus for the purification of waste air containing biologically decomposable impurities while U.S. Pat. No. 1,701,825 to Seil discloses a gas purification process that uses certain bacteria to treat a gas stream. Both of these references, however, are limited to treating specific compounds. Further, as will be made apparent from the following description, various features and aspects of the present invention remain absent from the prior art.

BRIEF DESCRIPTION OF THE DRAWINGS

Certain aspects of the invention are presented in the drawings as follows.

DETAILED DESCRIPTION

The "BIONITE", "BIODENITE" or "BIOVOC" scrubbers are a combination of a scrubber and a bioreactor to absorb target pollutants and convert them to nitrate, nitrogen or carbon dioxide and other resultant innocuous products using a suspended growth biochemical process. The suspended growth biochemical process is more efficient and responds better to fluctuating process parameters than an attached growth biochemical process. A constant and relatively low concentration of dissolved pollutant in the scrubbing solution results from biochemical reaction.

The scrubber consists of a scrubber section and a reactor section and is preferably based on the following reaction mechanisms.

Bionitrification Reaction $$NH_3+H_2O=NH_4^++OH^-$$

$$NH_4^++O_2+\text{Nitrifying bacteria}=NO_3^-+H_2O$$

Biondenitrification Reaction $$NO_3^-+\text{Organic Carbon}+\text{Nutrients}+\text{Denitrifying bacteria}=N_2+CO_2+H_2O$$

Organic Carbon (VOC) Reaction $$VOC+\text{Nutrients}+O_2+\text{Activated sludge bacteria}=CO_2+H_2O$$

These reactions are known (*Waste Treatment and Disposal*, Metcalf & Eddy, 1981) and have been used in the treatment of wastewater.

The above gaseous pollutants are removed from a waste gas stream by contacting the waste gas stream in the absorption tower with an aqueous suspension containing microorganisms. For maximum efficiency, according to the present invention, the aqueous suspension should be formed and modified based on the particular gaseous pollutant that is to be decomposed and removed from the waste gas stream.

For instance, in one embodiment, activated sludge containing various populations of microorganisms can be obtained from a number of different sources, including any waste water treatment facility. According to the present invention, once obtained, the activated sludge is mixed with water, if necessary, and placed in a reaction chamber. The waste gas stream to be processed or, alternatively, a gas stream containing the targeted gaseous pollutant or pollutants is fed slowly to the reaction chamber.

As the gas stream is fed slowly to the reaction chamber, microorganisms capable of breaking down the targeted gaseous pollutant or pollutants will begin to feed on such pollutants. As the microorganisms feed on the targeted pollutants, they will begin to multiply and thrive within the reaction chamber. Other microorganisms contained within the activated sludge that are not adapted to break down the targeted pollutants will, on the other hand, die for lack of food.

During this initial start up period, portions of the aqueous suspension are preferably removed and disposed of at periodic intervals for removing the dead microorganisms. Once a particular portion of the aqueous suspension is removed, make-up water can be added to the suspension in order to maintain a desired volume level. As portions of the aqueous suspension are removed, the dead microorganisms are taken out of the aqueous suspension while, simultaneously, the microorganisms feeding on the targeted gaseous pollutants continue to multiply and thrive. Ultimately, through this process, a concentrated aqueous suspension is formed that is extremely efficient in removing the targeted gaseous pollutants from a waste gas stream.

The absorption tower that may be used with the formed aqueous suspension can, in one embodiment, include the following components:

A. Scrubber Tower

The scrubber tower is a column containing internal scrubbing plates, such as segmented baffle plates or sieve trays, a liquid inlet distributor, a gas inlet and outlet and a demister. The design of the scrubber internals provide an unrestricted flow path for the scrubbing liquid and the treated gases. The configuration of plates inside the tower is such that liquid from the upper plate falls on to the lower plate and so on to the bottom. The falling liquid from each plate provides the interfacial area for mass transfer.

The scrubbing liquid is a biomass slurry which is continuously circulated using a recirculating pump. In one preferred embodiment, the recirculating pump is a centrifugal pump with an impeller speed of, for instance, at least 1,750 rpm. The recycle rate of the aqueous suspension should be such that the turnover of the biomass chamber volume occurs in a time ranging from about 0.1 hours to about 2 hours. Using centrifugal pumps with high impeller speeds and having quick turnover times produces a finely dispersed bacteria population that is not only well adapted to treating a gas stream but also prevents clogging of the scrubbing trays.

The biomass is composed of a mixture of bacteria and other microorganisms which biochemically oxidize dissolved $NH_4$ and VOC or biochemically reduce $NO_x$. Biomass slurry is pumped from the bottom of the bioscrubber and returned to the top of the tower. An $NH_3$, $NO_x$ or VOC laden gas stream is introduced at the bottom of the tower and flows upward around the scrubbing plates and through the falling biomass slurry. The pollutants are absorbed into the biomass slurry and the clean gas is discharged through the outlet duct of the scrubber tower. The biomass oxidizes or reduces the subject compound according to the above-cited reactions.

B. Pumping and Reaction Section

In preferred embodiments, the bottom section of the scrubber tower, referred to as the reactor, expands and forms a chamber containing an inventory of the biomass slurry. The size of the reactor section is dependent upon the total loading of the treated compounds and the variability of the loading. Oxygen may be supplied to the "BIONITE" and the "BIOVOC" scrubbers as a part of the gas mixture containing the $NH_3$ or VOC. An additional source of air may be required if the treated gas contains an insufficient amount of oxygen. Nutrients such as $PO_4$ and trace metals will often be metered into the reactor based on the process operating conditions. The biochemical oxidation of $NH_3$ consumes alkalinity and supply of alkalinity may be required. In the case of treating a VOC gaseous stream, an addition of ammonia and $PO_4$ may be needed.

In case of treatment of an $NO_x$ gaseous stream in the "BIODENITE" scrubber, addition of organic carbon, nutrients and pH control may be needed.

In the case of $NH_3$ treatment, nitrate accumulates in the reactor as a result of nitrification. High levels of nitrate will lead to inhibition of the nitrification reaction. Therefore, a nitrate blowdown may be utilized to maintain nitrate concentration inside the reactor below inhibitory levels.

Dead and decaying bacteria also accumulate in the reactor which must be wasted periodically. The design of the reactor may be such that biomass wasting and nitrate blowdown can occur together. The blowdown rate depends on the mean cell residence time (MCRT) of the bacteria and the maximum allowable nitrate concentration in the reactor.

The blowdown from the "BIONITE" scrubber containing waste biomass and nitrate may also be further treated in a biodenitrification reactor (see below).

C. Nutrient Feed System

The bacteria require nutrients such as $PO_4$, organic carbon (in case of $NO_x$ treatment) and ammonium (in case of VOC treatment) and several trace metals for their growth. Nutrients are metered into the reactor to provide optimal conditions for the biochemical process. The feed rate of the nutrients is dependent on the biomass concentration and other process conditions.

D. Air Supply System

Oxygen necessary for the "BIONITE" and "BIOVOC" scrubbers is supplied either as a part of the treated gas mixture or a supplemental source of air is provided. A dissolved oxygen meter may be situated in the reactor to control the amount of air flow by, for example, maintaining 4 mg/L dissolved oxygen concentration. The "BIODENITE" scrubber process is based on an anoxic biochemical reaction and the anoxic conditions can be maintained by the addition of a reducing agent based on dissolved oxygen and reduction/oxidation potential measurement and control.

E. Biodenitrification Reactor (As a Part of "BIONITE" Scrubber)

Blowdown from the "BIONITE" scrubber may be discharged into a denitrification bioreactor.

The denitrification reactor is preferably a completely mixed anoxic reactor containing denitrifying bacteria in suspension. The nitrate in the blowdown is reduced to nitrogen gas according to the biochemical reaction presented above.

The organic carbon source for denitrification may either be supplied through an external carbon source (e.g., methanol, acetate, acetone, etc.) or by acclimating the bacteria to use the dead biomass in the blowdown (internal carbon source). Using an external carbon source may provide higher denitrification rates (smaller reactor), but also higher operating cost versus using the internal carbon source which may lower the denitrification rate (larger reactor), but reduced operating cost. Hence, the choice of the carbon source (internal or external) will depend on the denitrification process kinetics, reactor design and economic factors.

F. Waste Sludge Filtration

Dead and decaying denitrifying bacteria must be periodically wasted from the reactor. The wasted sludge is filtered, dried and disposed off site or alternatively it may also be discharged to the sewer. The filtrate may either be returned to the bioreactor or discharged to the sewer.

G. Food to Microorganism Ratio

It has been unexpectedly discovered that the apparatus of the present invention operates very efficiently in comparison to prior art systems. For instance, conventional activated sludge systems for treating waste water typically operate at a food to microorganism ratio of from about 0.05 to about 0.6 kilogram BOD per kilogram of microorganisms per day. It has been discovered that the apparatus of the present invention, however, can operate at much higher rates. For instance, systems treating a VOC containing gas stream according to the present invention have been found to operate at food to microorganism ratios greater than 0.9 kilograms BOD per kilograms microorganisms per day. Thus, in comparison to conventional systems, the present invention can treat a greater quantity of pollutants using a lesser amount of microorganisms.

Figure 1:
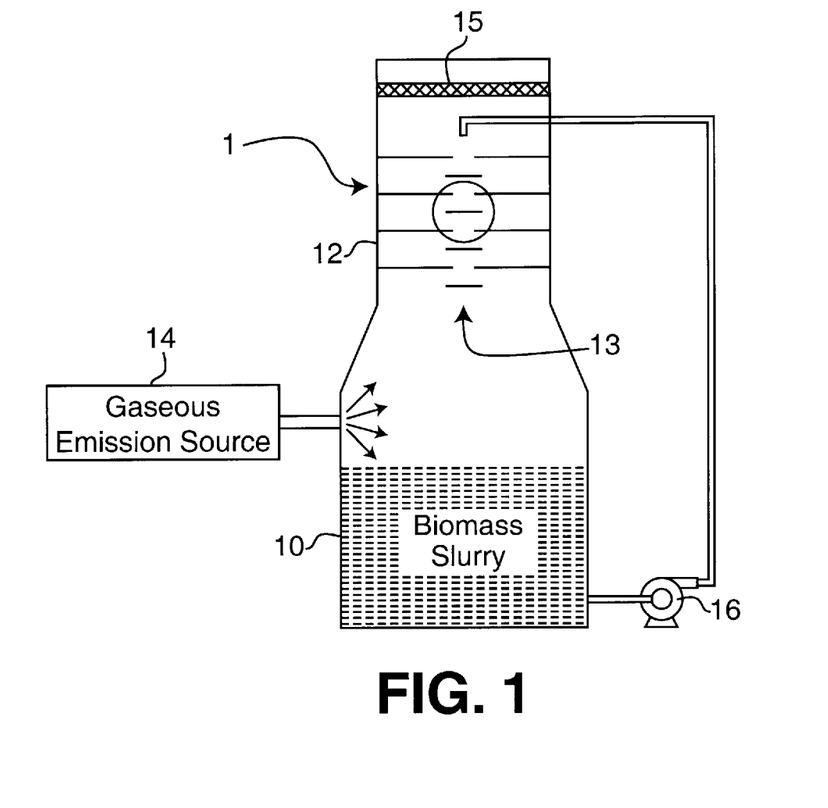
FIG. 1 is a schematic view of one embodiment of an apparatus for treating a waste gas stream in accordance with the present invention.
Figure 2:
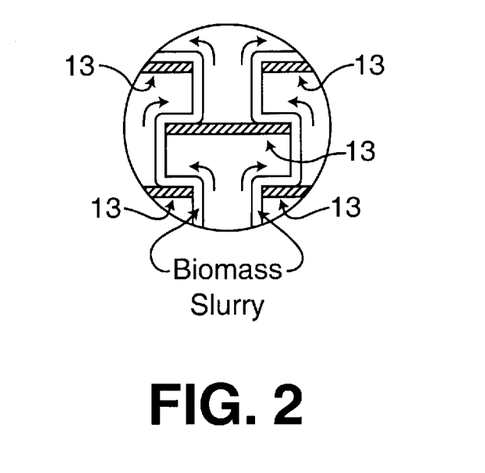
FIG. 2 is an enlarged cutaway portion of FIG. 1 illustrating of a series of baffles.

Referring to FIGS. 1 and 2, one embodiment of an absorption tower generally 1 for use in the process of the present invention in treating waste gas streams is illustrated. As shown, absorption tower 1 has an enlarged lower portion or biomass chamber 10 extending into an upper tower portion 12. Biomass chamber 10 holds an aqueous suspension or biomass slurry, containing microorganisms suitable for removing a targeted gaseous pollutant or pollutants from a waste gas stream. Upper portion 12 contains a series of scrubbing plates generally 13. In this embodiment, scrubbing plates 13 are segmented baffle plates defining a circuitous or labrithine path through which a waste gas from a gaseous emissions source 14 will travel. In an alternative embodiment, however, scrubbing plates 13 can be sieve trays which are trays containing a plurality of holes. After passing through plates 13, the gas will pass through a demister 15 that removes liquid droplets before the gas exits to the ambient environment.

The biomass slurry is continuously circulated by a pump 16 from biomass chamber 10 to a location above plates 13 in upper portion 12 of absorption tower 1. The slurry will thus flow over the plates before eventually returning to biomass chamber 10. As shown in FIG. 2, the flow of the slurry over the plates creates a waterfall effect, with the slurry from an upper plate landing on the surface of a plate immediately below. The waste gas stream is forced to travel through the flowing slurry on its way to the ambient environment.

When the gas contacts a slurry in this manner, the pollutants will be absorbed into the aqueous suspension and the bacteria will then ingest the particular compound or pollutant that is to be decomposed. Typically, the compound will be converted by the bacteria to some other compound which may or may not be suitable for immediate release into the atmosphere. If this compound is not suitable for immediate release, it may be reacted further using additional reaction mechanisms to achieve a compound which may be released.

FIGS. 3 through 6 will now be described with reference to various embodiments of the present invention that are directed to treating particular gaseous pollutants. Like reference numbers will be used to indicate similar elements in the different embodiments.

Figure 3:
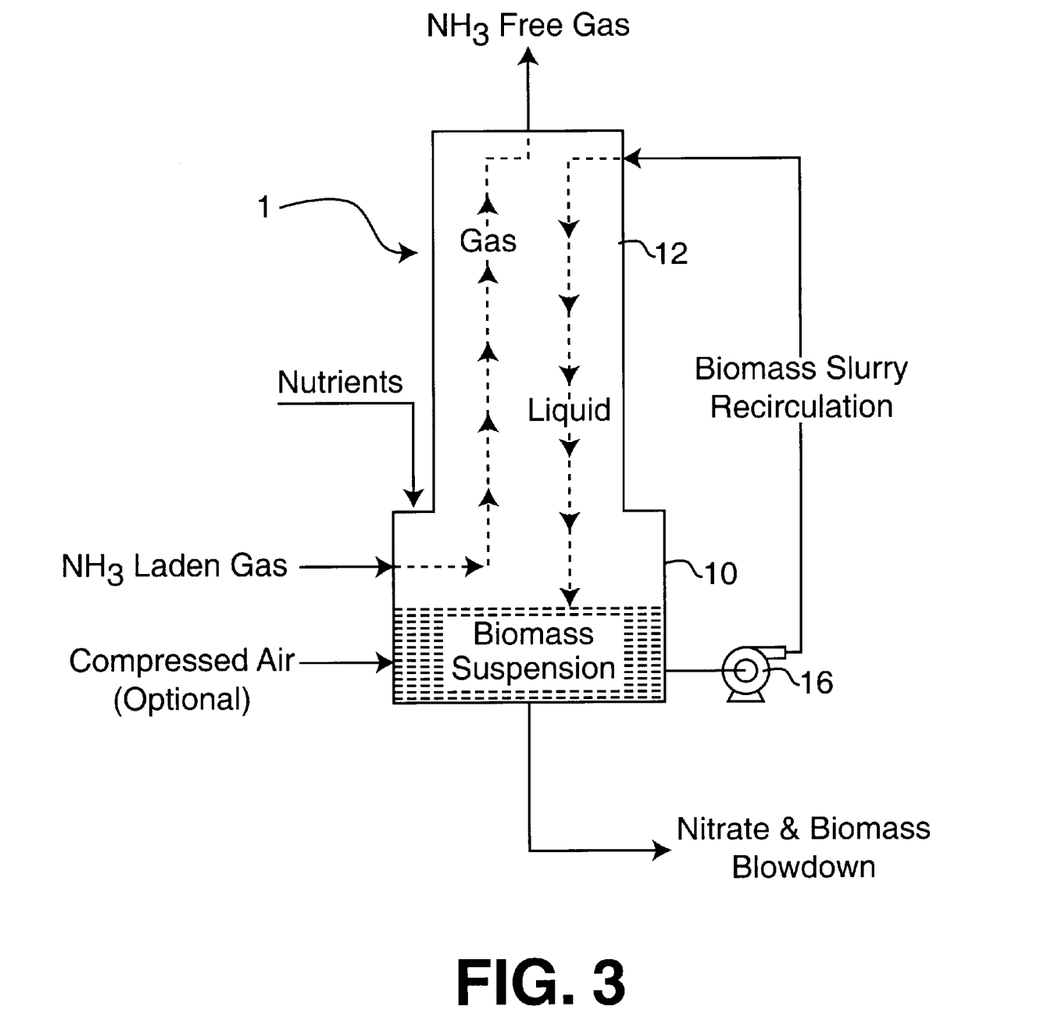
FIG. 3 presents a process flow diagram for control and treatment of gaseous emissions of $NH_3$.

Referring to FIG. 3, one embodiment of a process for removing ammonia from a waste gas stream is illustrated. As shown, a gas stream containing ammonia is fed through absorption tower 1 where it is contacted with a biomass suspension. The biomass suspension contains microorganisms which remove ammonia from the waste gas stream and convert it to nitrate and nitrite. The formed nitrate and nitrite accumulates within the biomass suspension and can be removed during periodic blowdowns.

Treating ammonia laden gas streams is particularly a problem in many chemical industries. For instance, waste gas streams containing ammonia can be produced during the production of various chemicals, such as organic amines, at textile dye houses, at metal coating facilities, and at various other production facilities. The process of the present invention is particularly well suited for use at any such production site where gaseous ammonia is produced and must be treated before the gas stream can be emitted to the environment.

In order to break down ammonia, the microorganisms present in the biomass suspension require oxygen and water. In this regard, if the gas stream being produced does not contain sufficient levels of oxygen, an oxygen source such as compressed air, can be fed to the biomass suspension within biomass chamber 10.

Besides oxygen, it is also beneficial to add various nutrients to the biomass suspension during the process. In particular, the biomass suspension should be fed trace metals and a phosphorous source such as various phosphates. Further, in some applications involving denitrification, a carbon source must also be added to the biomass suspension, particularly when the gas stream being treated does not contain organic compounds. Carbon can be supplied to the microorganisms by adding, for instance, acetone, an alcohol or an acetate to the suspension.

As described above, ammonia is broken down by the microorganisms into nitrates and nitrite. When produced, nitrite can combine with the biomass suspension to form an acid. Acidifying the biomass suspension, however, may have an adverse effect on the microorganisms. Thus, in one embodiment, an alkaline material is preferably fed to the biomass suspension during the process in order to keep the pH of the suspension in a range of from about 6.5 to about 9.0. The alkaline material that can be fed to the biomass suspension can include, for instance, sodium hydroxide or sodium carbonate. In one embodiment, biomass chamber 10 can be equipped with a pH controller which senses the pH of the biomass suspension and automatically feeds an alkaline material to the suspension for maintaining the suspension in the desired pH range.

Besides forming an acid, the byproducts of the ammonia reaction also tend to inhibit further reaction of the microorganisms with ammonia if the byproducts become concentrated within the biomass suspension. Consequently, portions of the biomass suspension must be removed periodically in order to prevent nitrate and nitrite concentrations from becoming to high.

In waste water systems that treat ammonia, according to the "Nitrogen Control Manual" issued by the U.S.E.P.A., nitrification is supposedly inhibited when nitrite-nitrogen ($NO_2$—N) concentrations are above 280 ppm (mass). Unexpectedly, however, it has been discovered that the process of the present invention operates much more efficiently than liquid waste water systems that treat ammonia. In particular, it has been found that the system of the present invention will continue to effectively remove ammonia from a waste gas stream even when the nitrate-nitrogen concentration in the biomass slurry is above 600 ppm at a pH of about 7.2. It is not known why such beneficial results are achieved by the present invention, except for the fact that it appears that the process is simply much more efficient than conventional waste water treatment facilities.

The portions of the biomass suspension that are removed from biomass chamber 10 in order to lower nitrate concentrations can, in one embodiment, be fed directly to a sewer if the particular facility does not have a government mandated nitrate limit.

Figure 4:
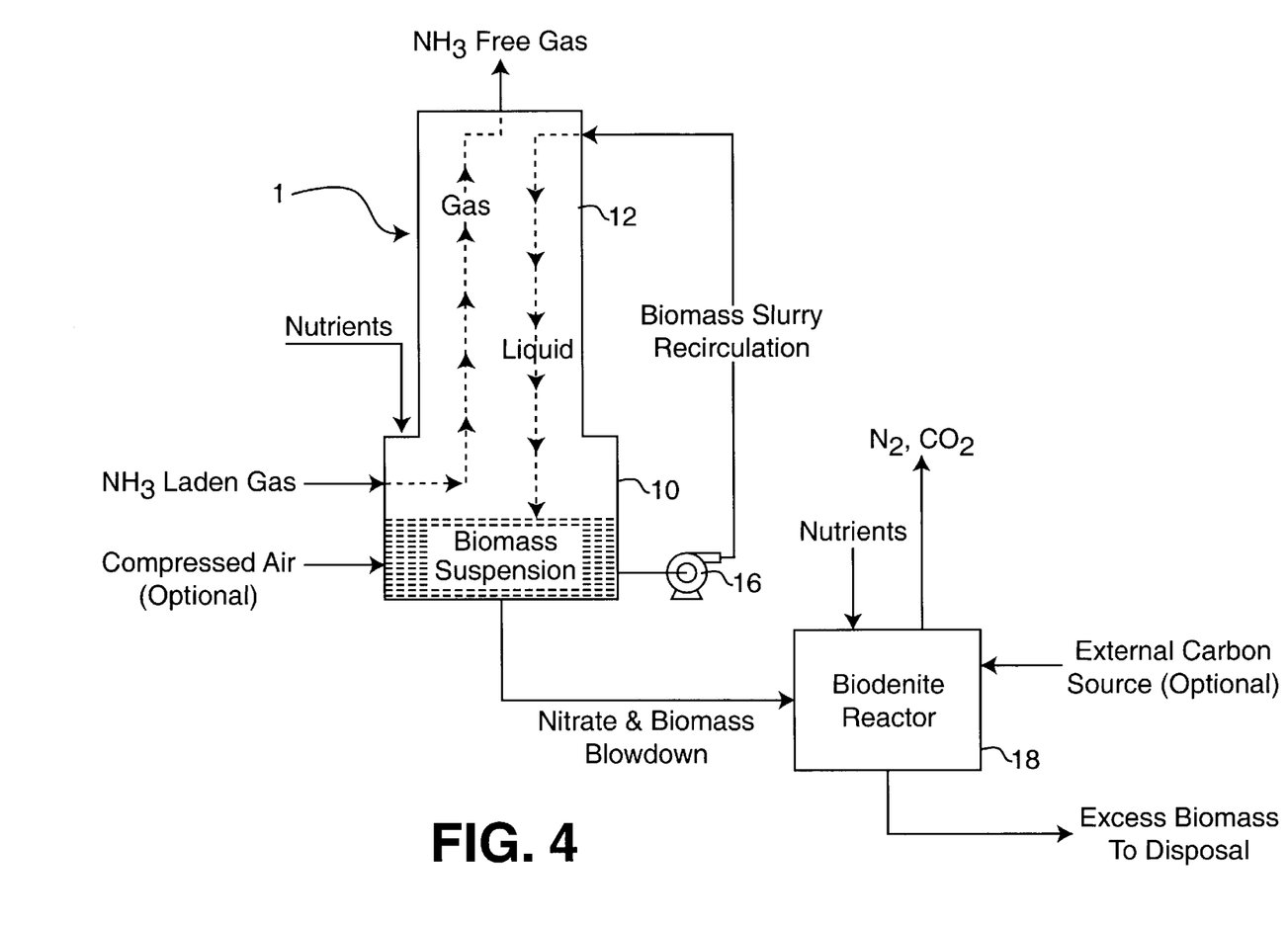
FIG. 4 presents a process flow diagram for control and treatment of gaseous emissions of $NH_3$ followed by biochemical reduction of nitrate in the liquid waste stream using a suspended growth "BIONITE" scrubber.

In an alternative embodiment, however, as illustrated in FIG. 4, the portions removed from the biomass suspension can be fed to a biodenite reactor 18. Reactor 18, in this embodiment, contains a second aqueous suspension that includes microorganisms particularly well adapted for removing nitrates (and other oxides of nitrogen if present) from a waste water supply. In particular, the microorganisms contained in reactor 18 are capable of removing oxygen from nitrates and converting the nitrates into nitrogen which, as shown, can be released to the atmosphere.

The reaction that takes place between the microorganisms and the nitrates is an anoxic reaction. Thus, the second aqueous suspension contained in reactor 18 should be maintained with low oxygen levels in order to promote decomposition of the nitrates. In this regard, if necessary, an oxygen scavenger can be added to the second aqueous suspension.

Besides maintaining low oxygen levels, the microorganisms contained in reactor 18 should be fed nutrients during the process, including trace metals and phosphates. Also, if not contained in the portions of the biomass suspension that are fed to reactor 18, it may also be desirable to add a carbon source to reactor 18 which is a required food source for the microorganisms. Carbon can be supplied to the microorganisms by feeding to reactor 18 a carbon containing compound, such as methanol, an acetate, or acetone.

Once the waste water fed to reactor 18 is treated by the microorganisms and after a substantial portion of the nitrates have been converted to nitrogen and carbon dioxide, the treated waste water can then be disposed of as desired.

Figure 5:
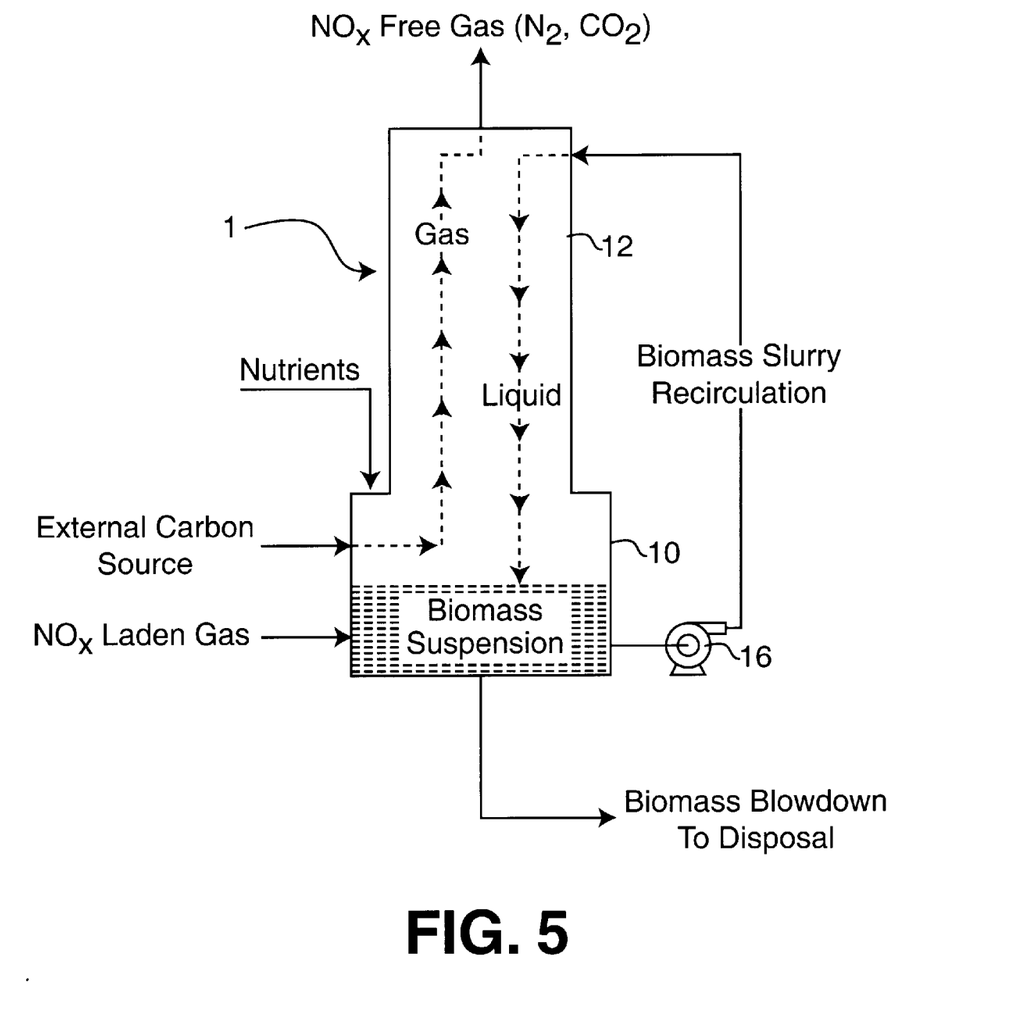
FIG. 5 presents a process flow diagram for control and treatment of gaseous emissions of $NO_x$ using the suspended growth "BIODENITE" scrubber.

Referring to FIG. 5, an alternative embodiment of a process in accordance with the present invention is illustrated. In particular, absorption tower 1 in FIG. 5 is adapted for the removal of oxides of nitrogen from a waste gas stream. In this embodiment, the biomass suspension contains microorganisms which break down oxides of nitrogen into nitrogen and carbon dioxide. As shown, an external carbon source may need to be supplied to the biomass suspension if low levels of carbon are contained in the waste gas stream being treated. Similar to biodenite reactor 18, the carbon source can be supplied to the microorganisms by feeding to the biomass suspension a carbon compound, such as methanol, an acetate, acetone, or the like.

In this embodiment, the microorganisms operate under anoxic conditions to remove oxygen from the oxides of nitrogen in converting them to nitrogen gas. Thus, the biomass suspension should be maintained at lower oxygen levels.

As shown, nutrients such as trace metals and phosphates can also be fed to the biomass suspension for creating optimum conditions for the microorganisms.

In this embodiment, since oxides of nitrogen generally have a lower water solubility limit than many other gases, the waste gas stream to be treated is preferably fed directly into the biomass suspension for promoting better contact between the gas stream and the suspension.

Figure 6:
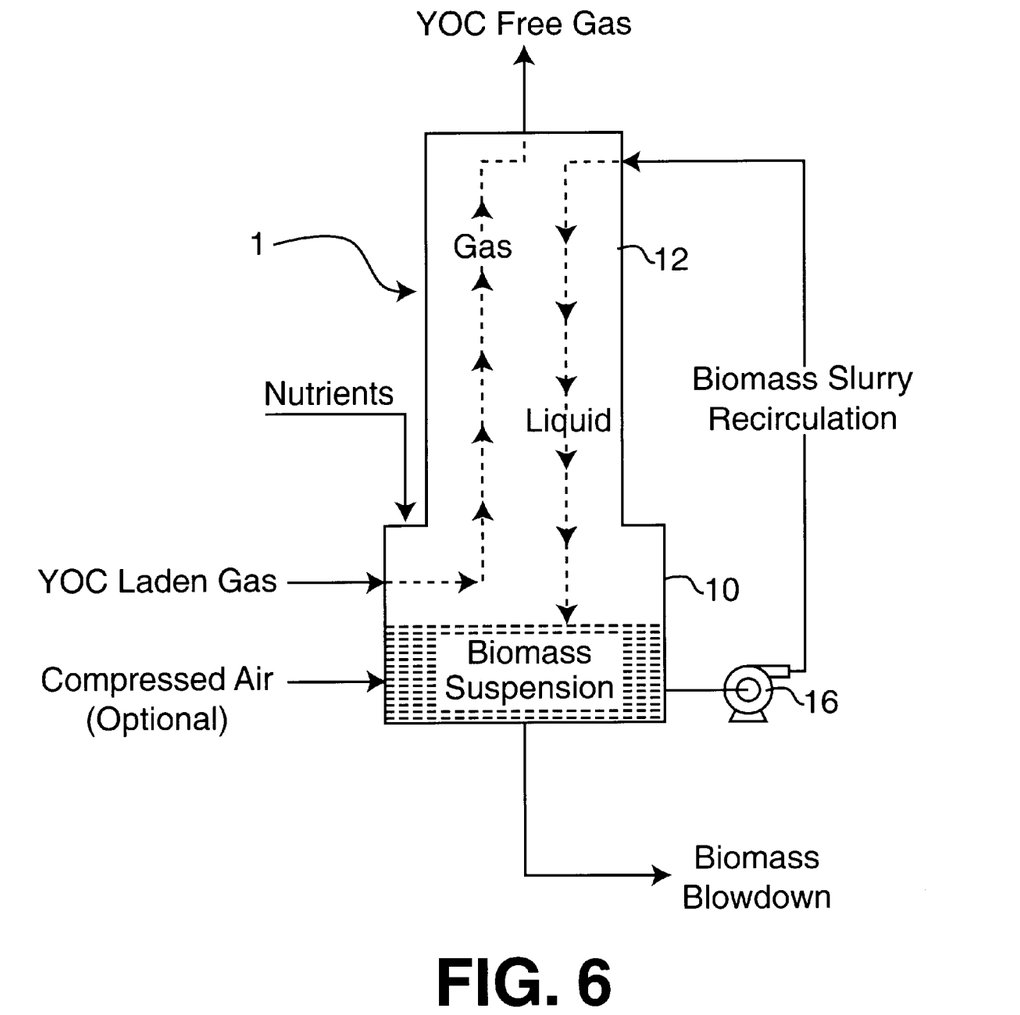
FIG. 6 presents a process flow diagram for control and treatment of gaseous emissions of VOC using the suspended growth "BIOVOC" scrubber.

Absorption tower 1 can also be used for removing volatile organic compounds from a waste gas stream as illustrated in FIG. 6. For instance, a partial list of treatable volatile organic compounds that may be treated according to the present invention include the following:

Alcohols: methanol, ethanol, isopropanol

Ketones: acetone, ethylketone, methylethylketone

Amines: ethylamine, triethylamine, hexamethylenetetramine, ethylene diamine

Aldehydes: formaldehyde, acetaldehyde

Carboxylate groups: formate, acetate, acrylate

Aromatics: benzene, toluene, ethylbenzene, styrene

When contacted with the microorganisms within the biomass suspension, the volatile organic compounds are converted to carbon dioxide and water.

When treating volatile organic compounds, it may be necessary to feed to the biomass suspension an oxygen source and a nitrogen source, if such elements are not contained in the waste gas stream being treated. A preferred nitrogen source that may be fed to the biomass suspension is ammonia.

Similar to the other systems, preferably nutrients, such as trace metals and phosphates are also fed to the suspension for use by the microorganisms.

In one preferred embodiment of the present invention, absorption tower 1 is used to treat one or more gas streams containing ammonia in combination with volatile organic compounds. Various benefits and advantages are obtained by combining the treatment of ammonia and volatile organic compounds within one absorption tower. For instance, through the process of the present invention, both types of pollutants can be removed from the waste gas stream efficiently without the need for multiple systems.

Also of advantage, by treating volatile organic compounds in combination with ammonia, the microorganisms used to decompose both pollutants will work together synergistically. In particular, as described above, the microorganisms used to break down volatile organic compounds typically need a nitrogen source. In this embodiment of the present invention, the nitrogen source can come from the ammonia contained in the waste gas stream, eliminating the necessity of having to add a nitrogen source to the biomass chamber.

Besides treating multiple waste gas streams containing different types of pollutants, the process of the present invention is also well adapted to simultaneously treating a waste gas stream and a waste water stream. The waste gas stream and the waste water stream can contain the same pollutant to be treated or can contain various different pollutants. For instance, in a similar arrangement to the embodiment described above, the waste gas stream and the waste water stream can both contain ammonia and volatile organic compounds that can be decomposed by the microorganisms contained within the biomass suspension.

When treating a waste water stream in combination with a waste gas stream, the waste water stream can be continuously or intermittently fed to the biomass chamber. The microorganisms contained within the biomass suspension can then break down any pollutants contained within the waste water. In this embodiment, it may be necessary to periodically or continuously remove larger portions of the biomass suspension, depending upon the flow rate and quantity of the waste water being treated.

When removing the treated waste water from the biomass chamber in larger quantities, the removed liquid can be filtered in order to prevent large quantities of the microorganisms from being removed from the biomass suspension. For instance, in one embodiment, as waste water is fed to biomass chamber 10, an equal portion of liquid from the biomass suspension can be removed by being filtered through a microfilter which is permeable to liquids but is impermeable to microorganisms. In this manner, an effective concentration of microorganisms is always maintained within the suspension.

Besides using a microfilter, the excess liquid can also be removed from the biomass suspension using a clarifier. A clarifier refers to a device that only removes top portions of a liquid volume for preventing substantial amounts of solids, such as microorganisms, contained within the liquid from being removed. When using a clarifier, typically a settling tank will be required for allowing the microorganisms to settle within the suspension prior to removing top portions of the liquid.

Treating a waste gas stream simultaneously with a waste water stream would simplify many treating systems at various chemical processing plants. For instance, in one embodiment, one system can be used to both treat a waste gas stream being produced at an industrial site in combination with a sanitary waste water stream also being produced at the same site.

Figure 7:
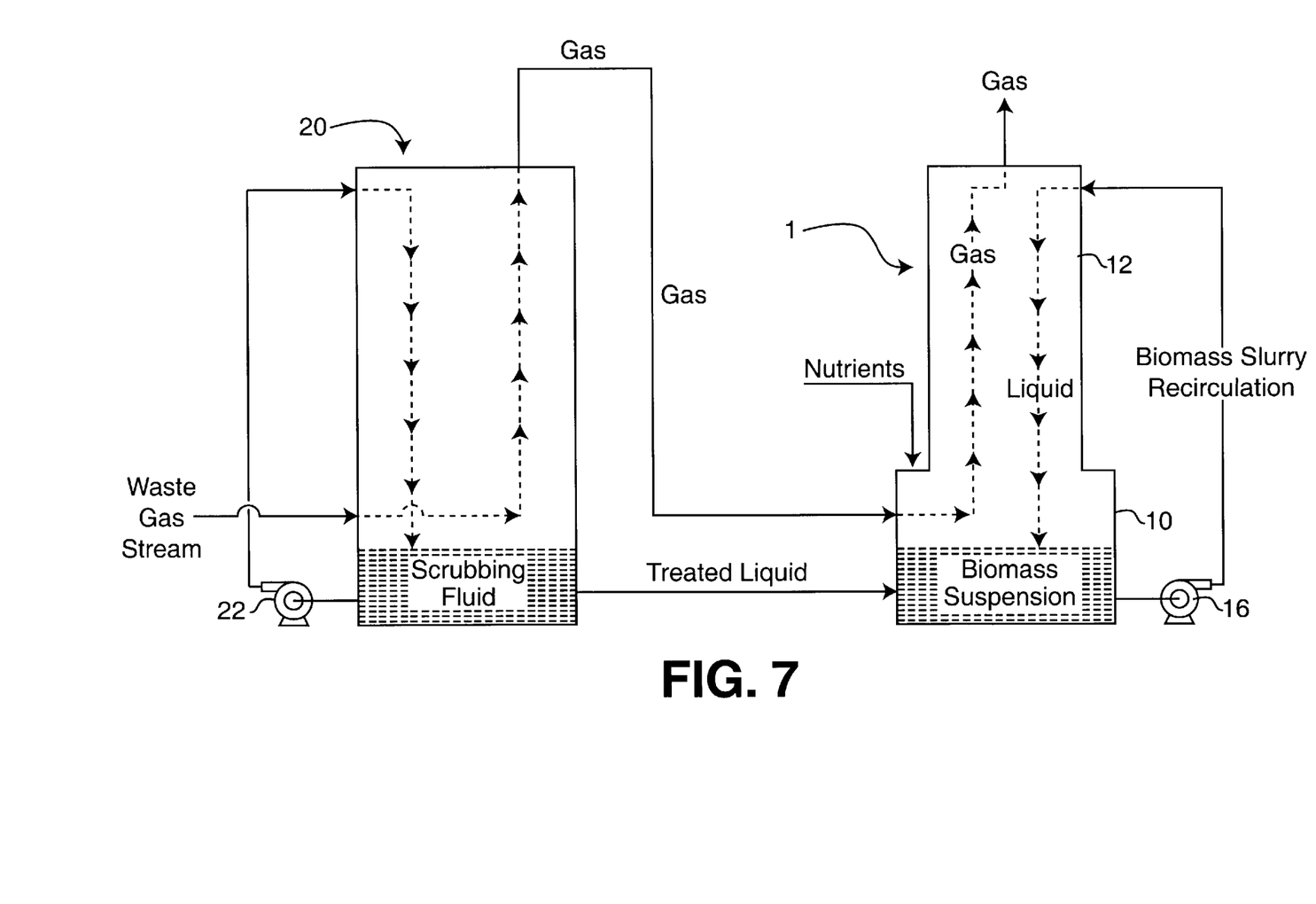
FIG. 7 is a schematic view of one embodiment of an apparatus and process according to the present invention for washing a waste gas stream prior to treatment in an absorption tower.
Figure 8:
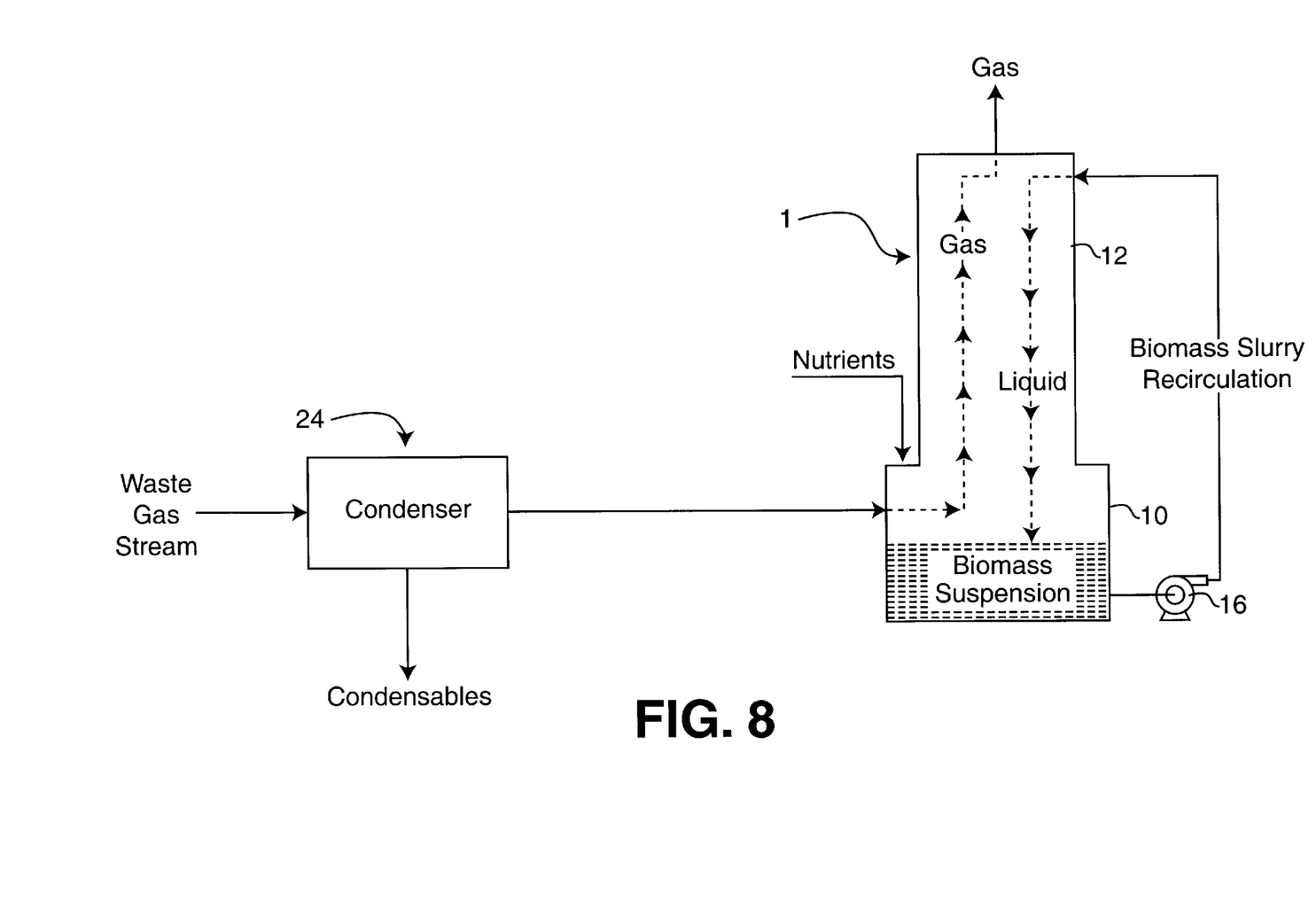
FIG. 8 is a schematic view of one embodiment of an apparatus and process for condensing reusable components from a waste gas stream prior to treating the waste gas stream in an absorption tower in accordance with the present invention.

Referring now to FIGS. 7 and 8, two other further embodiments of the present invention are illustrated. FIG. 7 is directed to using absorption tower 1 in combination with a liquid washing chamber generally 20. As shown, washing chamber 20 contains a scrubbing fluid such as water which is circulated by a pump 22 from the bottom of chamber 20 to the top of the chamber 20. At the top of chamber 20, the scrubbing fluid is dispensed into the chamber where it contacts a waste gas stream traveling upwards through the chamber as shown. The scrubbing fluid absorbs portions of pollutants contained within the gas stream.

For instance, if the gas stream contains ammonia and/or volatile organic compounds, the ammonia or the volatile organic compounds can be partially solubilized and collected in chamber 20. The remaining washed gas stream can then be fed to absorption tower 1 as shown in the figure.

In one embodiment, when treating a waste gas stream containing ammonia, the scrubbing fluid used in washing chamber 20 can be an aqueous solution that has been acidified in order to remove larger portions of the ammonia from the gas stream. For instance, the scrubbing fluid can be an aqueous solution having a pH of less than about 6, and particularly from about 4.0 to about 5.0. The acidified scrubbing fluid can be made by adding any suitable acid, such a sulfuric acid, to an aqueous solution.

The scrubbing fluid collected in chamber 20 can then be fed to absorption tower 1. For instance, in one embodiment, the scrubbing fluid can be fed continuously at a constant rate to the biomass chamber. Any pollutants contained within the scrubbing fluid can be degraded by microorganisms contained in the biomass suspension within biomass chamber 10.

The arrangement illustrated in FIG. 7 is designed to maintain a continuous and uniform pollutant concentration being fed to absorption tower 1, even when the pollutant concentration in the waste gas stream fluctuates. In particular, when greater concentrations of pollutants are present in the waste gas stream, greater concentrations of the pollutants are washed from the gas stream and collected within the scrubbing fluid. As described above, the scrubbing fluid can then be fed at a constant rate to absorption tower 1. Thus, the rate at which the pollutants are fed to absorption tower 1 for treatment remains more uniform and constant. By being able to handle wide fluctuations in pollutant concentration, the size of the absorption tower can be minimized.

Besides being used to remove volatile components from the waste gas stream, washing chamber 20 can also be used to break down components within the waste gas stream so that the waste gas stream can be subsequently processed by the biomass suspension. For instance, in one embodiment, the waste gas stream may contain organic amines, such as hexamine. In this embodiment, washing chamber 20 can be used to contact the organic amine with a solution that converts the organic amine into degradable components. For example, hexamine can be broken down into ammonia and formaldehyde, which can then be subsequently treated within absorption tower 1 by the biomass suspension.

For instance, a waste gas stream can be fed to washing chamber 20 where it is contacted with an acidic solution having a pH of from about 4 to about 5. For instance, the washing solution can be an aqueous solution of sulphuric acid, or any other suitable acid.

Once contacted with the waste gas stream, the acidic solution contained in chamber 20 absorbs and then converts hexamine into ammonia and formaldehyde. The acidic scrubbing solution can then be fed to biomass chamber 10 wherein the ammonia and formaldehyde are decomposed by microorganisms contained within the biomass suspension, similar to the processes described above. In this arrangement, the hexamine is converted into non-hazardous components which can be safely released to the atmosphere.

Referring to FIG. 8, a further embodiment of the present invention is illustrated in which the waste gas stream being processed is first passed through a condenser generally 24 before being fed to absorption tower 1. In this embodiment, condenser 24 is used to remove reusable condensable components from the waste gas stream, before the waste gas stream is processed by the microorganisms within the biomass suspension. Preferably, condenser 24 is a heat exchanger that contacts the waste gas stream indirectly with a cooling fluid. As used herein, indirect contact means that heat transfer occurs between the two fluids without the fluids mixing. For instance, condenser 24 can be a shell and tube type heat exchanger.

The system illustrated in FIG. 8, for instance, is particularly well adapted for use in the wood products industry. For example, paper mills typically produce a waste gas stream that not only contains volatile organic compounds that must be removed but also contains condensables, such as turpentine in gaseous form. For example, condenser 24 can be operated at a particular temperature that condenses the turpentine from the waste gas stream without condensing significant amounts of unwanted volatile organic compounds. Once condensed, the turpentine can be collected and reused as desired. Of particular advantage, by removing the turpentine from the waste gas stream, less foaming occurs within biomass chamber 10.

The present invention may be better understood with reference to the following examples.

EXAMPLE NO. 1

The following pilot test was performed in order to demonstrate the efficiency of the apparatus and process of the present invention for removing methanol from a waste gas stream.

A pilot test was conducted using a methanol-air gas mixture. The pilot system consisted of a 70 gallon bioreactor and a 12" diameter tray tower. The tray tower consisted of 10 counterflow baffle trays. A centrifugal pump recirculated a biomass slurry through the tower and an ambient air blower aerated the contents in the bioreactor.

Figure 9:
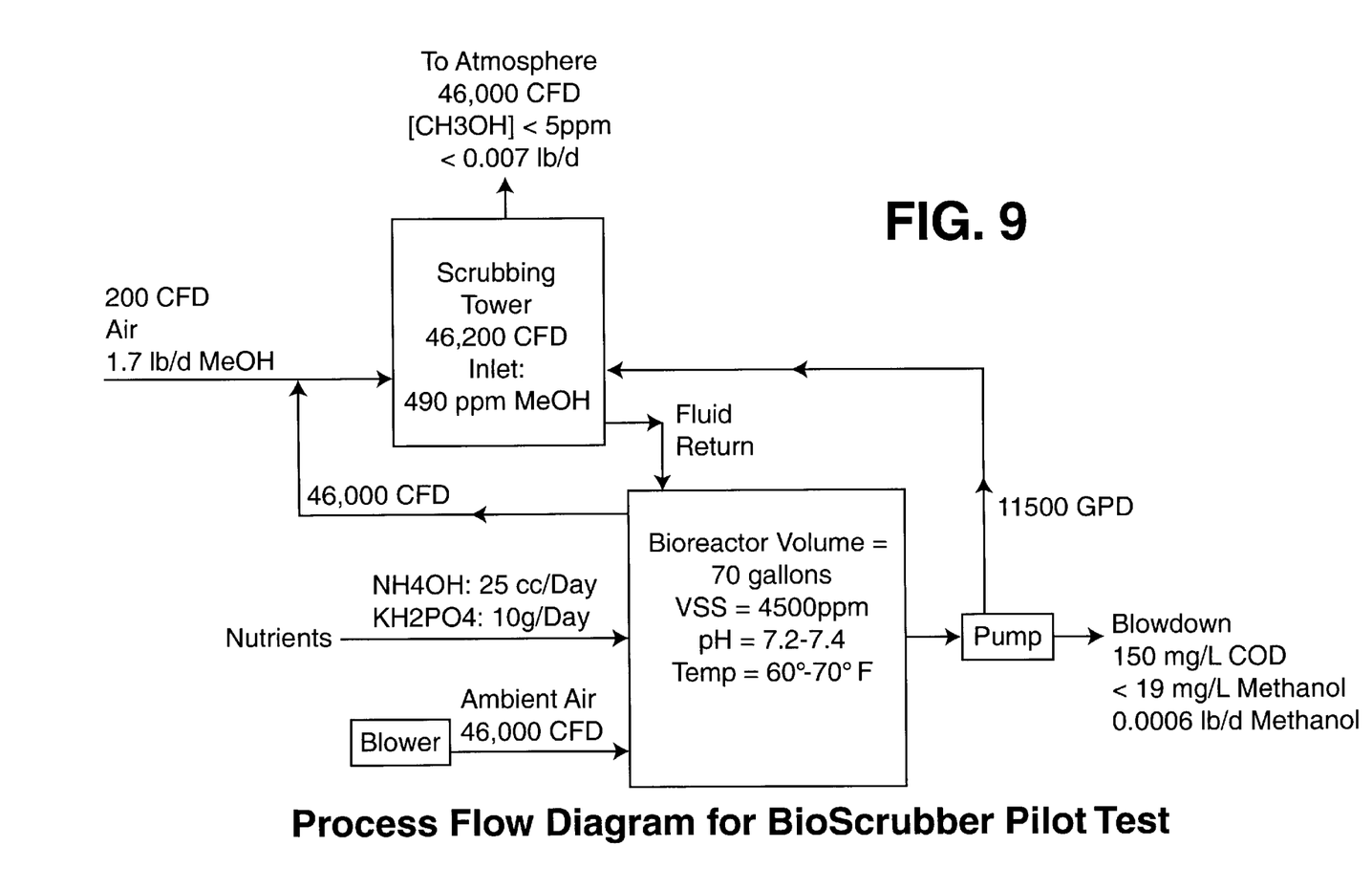
FIG. 9 is a schematic diagram of the process described in Example 1.

The performance of the pilot test is illustrated in FIG. 9. A methanol saturated air stream containing 1.7 lb methanol/day was fed to the scrubber tower. Greater than 98% removal of methanol was achieved through the scrubber tower. The methanol absorbed into the recirculating biomass slurry was subsequently oxidized to $CO_2$ and $H_2O$ in the bioreactor. The sludge blowdown from the reactor was approximately 7 gallons/day and contained <10 mg/L of unreacted methanol.

Relatively high methanol oxidation rates were observed in the bioreactor. Food-Microorganism ratios up to 1.0 lb methanol/lb ML VSS/day were easily attained. As the Food/Microorganism ratio varied from 0.5 to 1 lb methanol/lb VSS/day, the methanol concentration in the blowdown remained low and that in the exhaust was less than 5 ppm.

EXAMPLE NO. 2

Figure 10:
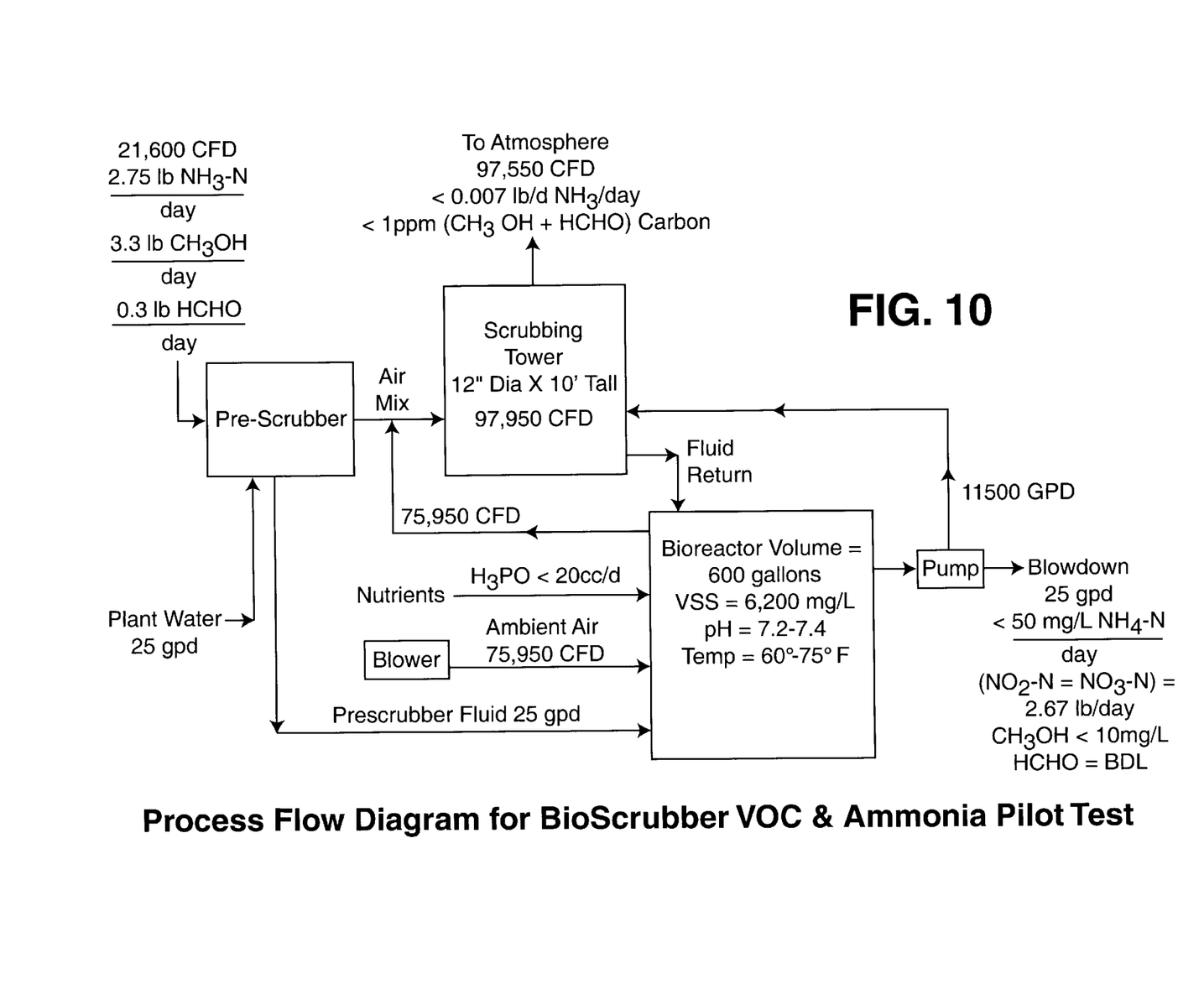
FIG. 10 is a schematic diagram of the process described in Example 2.

The following test was performed in order to demonstrate the efficiency of the process and apparatus of the present invention in removing both ammonia and a volatile organic compound (VOC) from a waste gas stream. A schematic diagram of the trial is illustrated in FIG. 10.

Field trials using a pilot scale system was conducted on a VOC and ammonia laden emission stream from a specialty chemicals manufacturing plant. The pilot system consisted of a water prescrubber, 600 gallon bioreactor and a 12" diameter tray tower. The tray tower consisted of 8 counterflow sieve trays. A centrifugal pump recirculated biomass slurry at a flow rate of 8 gpm through the tower and 45 scfm of ambient air was sparged to aerate the contents in the bioreactor. The pre-scrubber consisted of a 70 gallon tank mounted with 3 sieve trays. Water adjusted to a pH of 4 to 5 was recirculated at a flow rate of 9 gpm through the prescrubber. Inlet gas entered the prescrubber and exhausted into the tray tower. A metering pump transferred 25 gpd of liquid from the prescrubber tank to the reactor tank. The same volume of sludge from the reactor was discharged as blowdown. The prescrubber helped dampen wide fluctuations in the ammonia emissions in the inlet gas stream and provided a stable ammonia feed to the bioreactor. The prescrubber-absorption tower system was operated at various gas flow rates in order to develop process design and scale-up parameters.

The emission stream consisted of ammonia in addition to VOC's such as methanol and formaldehyde. Greater than 99.5% of ammonia was removed from the gas stream. The absorbed ammonia was subsequently oxidized to nitrate and nitrite in the bioreactor. About 2.75 lb/day of ammonia was fed to the absorption tower and was converted to nitrate and nitrite in the bioreactor. As the ammonia loading rate varied from 0.035 to 0.09 lb NH3/lb ML VSS/day, the blowdown NH4–N varied from 0–30 mg/L and exhaust NH3 concentration from 0–5 ppm. Nitrate and nitrite that were formed as a result of ammonia oxidation were discharged along with the blowdown.

Greater than 99% methanol and formaldehyde were also removed through the scrubber tower. The absorbed methanol and formaldehyde were subsequently oxidized in the bioreactor tank to $CO_2$ and $H_2O$. The sludge blowdown contained negligible concentration of formaldehyde and <10 mg/L of unreacted methanol.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method for removing ammonia from a waste gas stream, said method comprising the steps of:

provi ding an aqueous suspension containing microorganisms, said aqueous suspension being held in a biomass chamber;

circulating said aqueous suspension through an adsorption tower;

contacting a waste gas stream containing ammonia with said aqueous suspension within said absorption tower, said waste gas stream and said aqueous suspension flowing through said absorption tower countercurrently, said aqueous suspension removing said ammonia from said waste gas stream, said microorganisms contained within said aqueous suspension converting said ammonia to nitrates; and contacting said waste gas stream with a scrubbing fluid in a washing chamber prior to said waste gas stream entering said absorption tower, said scrubbing fluid removing portions of said ammonia from said waste gas stream, said scrubbing fluid being fed to said biomass chamber for degradation of said ammonia in said scrubbing fluid by said microorganisms.

2. A method as defined in claim 1, wherein said absorption tower includes a series of consecutive scrubbing plates positioned so as to provide a substantially unrestricted flow for said aqueous suspension.

3. A method as defined in claim 1, further comprising the step of periodically removing a portion of said aqueous suspension from said biomass chamber in order to remove dead microorganisms and nitrates from said aqueous suspension, said aqueous suspension contained in said biomass chamber being replenished with an aqueous make up solution.

4. A method as defined in claim 1, further comprising the step of adding oxygen to said aqueous suspension for use by said microorganisms.

5. A method as defined in claim 1, further comprising the step of adding an alkaline composition to said aqueous suspension for maintaining said aqueous suspension at a pH of from about 6.5 to about 9.0.

6. A method as defined in claim 1, wherein said aqueous suspension maintains a nitrite-nitrogen concentration greater than about 600 ppm.

7. A method as defined in claim 1, further comprising the step of feeding portions of said aqueous suspension to a liquid reactor, said liquid reactor including a second aqueous suspension containing denitrifying organisms, said denitrifying organisms converting nitrates contained in said portions of said aqueous suspension into nitrogen.

8. A method as defined in claim 1, wherein said waste gas stream further comprises volatile organic compounds, said aqueous suspension removing and degrading said volatile organic compounds from said waste gas stream.

9. A method as defined in claim 8, wherein said absorption tower operates at a food-to-microorganism ratio of grater than about 0.8 kilograms per BOD kilogram of microorganisms per day.

10. A method as defined in claim 1, wherein said aqueous suspension is circulated at a rate such that the total volume of said aqueous suspension is circulated between said biomass chamber and said absorption tower within a period of time of from about 0.1 hours to about 2 hours.

11. A method as defined in claim 1, wherein said scrubbing fluid comprises an acidic aqueous solution having a pH of less than about 6.

12. A method as defined in claim 11, wherein said waste gas stream further contains an organic amine, said acidic scrubbing fluid removing said organic amine from said waste gas stream and converting said organic amine into components degradable by said microorganisms contained in said aqueous suspension.

13. A method for removing oxides of nitrogen from waste gas stream, said method comprising the steps of:

providing an aqueous suspension containing microorganisms, said aqueous suspension being held in a biomass chamber;

circulating said aqueous suspension through an absorption tower;

contacting a waste gas stream containing oxides of nitrogen with said aqueous suspension within said absorption tower, said waste gas stream and said aqueous suspension flowing through said absorption tower countercurrently, said aqueous suspension removing said oxides of nitrogen from said waste gas stream, said microorganisms contained within said aqueous suspension converting said oxides of nitrogen to nitrogen; and contacting said waste gas stream with a scrubbing fluid in a washing chamber prior to said waste gas stream entering said absorption tower, said scrubbing fluid being fed to said biomass chamber for degradation thereof.

14. A method as defined in claim 13, wherein said absorption tower includes a series of consecutive scrubbing plates positioned so as to provide a substantially unrestricted flow path for said aqueous suspension.

15. A method as defined in claim 13, further comprising the step of adding carbon to said aqueous suspension for use by said microorganism.

16. A method as defined in claim 15, wherein carbon is supplied to said aqueous suspension by adding to said aqueous suspension a material selected from the group consisting of an alcohol, acetate, acetone, and mixtures thereof.

17. A method as defined in claim 13, further comprising the step of maintaining oxygen levels in said aqueous suspension at levels that promote anoxic metabolism of said oxides of nitrogen.

18. A method as defined in claim 13, wherein said aqueous suspension is circulated at a rate such that the total volume of said aqueous suspension is circulated between said biomass chamber and said absorption tower within a period of time of from about 0.1 hours to 2 hours.

19. A method for treating a waste gas stream comprising the steps of:

providing a waste gas stream containing at least one condensable component in gaseous form and least one gaseous pollutant;

condensing said at least one condensable component from said waste gas stream, thereby converting said at least one condensable component into a liquid;

separating said at least one condensable component from said waste gas stream in liquid form and collecting said at least one condensable component for reuse;

feeding said remaining waste gas stream into absorption tower, said waste gas stream contacting an aqueous suspension within said absorption tower, said aqueous suspension containing microorganisms that decompose said at least one pollutant contained in said waste gas stream; and wherein said at least one condensable component comprises a turpentine and said at least one pollutant contained in said gas stream comprising a volatile organic compound.

20. A method as defined in claim 19, wherein said absorption tower includes a series of consecutive scrubbing plates positioned so as to provide a substantially unrestricted flow path for said aqueous suspension.

21. A method as defined in claim 19, wherein said at least one condensable component is condensed from said waste gas stream by indirectly contacting said waste gas stream with a cooling fluid.

* * * * *